United States Patent [19]

Freeman et al.

[11] Patent Number: 4,555,934
[45] Date of Patent: Dec. 3, 1985

[54] METHOD AND APPARATUS FOR NONSTEADY STATE TESTING OF PERMEABILITY

[75] Inventors: David L. Freeman, Garland; Darrell C. Bush, Colleyville, both of Tex.

[73] Assignee: Core Laboratories, Inc., Dallas, Tex.

[21] Appl. No.: 426,798

[22] Filed: Sep. 29, 1982

[51] Int. Cl.[4] ............................................. G01N 15/08
[52] U.S. Cl. .......................................................... 73/38
[58] Field of Search ....................................... 73/37, 38

[56] References Cited

U.S. PATENT DOCUMENTS

| | | | |
|---|---|---|---|
| 2,633,015 | 3/1953 | Morris | 73/38 |
| 2,821,680 | 1/1958 | Slusser et al. | 73/38 |
| 2,842,958 | 7/1958 | Sayre et al. | 73/38 |
| 2,867,116 | 1/1959 | Aronofsky | 73/38 |
| 3,139,747 | 7/1964 | Ferrell | 73/38 |
| 3,199,341 | 8/1965 | Heuer et al. | 73/38 |
| 4,198,853 | 4/1980 | Graham | 73/38 |
| 4,198,854 | 4/1980 | Washington | 73/38 |
| 4,253,327 | 3/1981 | Wiley | 73/38 |

FOREIGN PATENT DOCUMENTS

| | | |
|---|---|---|
| 1192033 | 5/1970 | United Kingdom . |
| 1257835 | 12/1971 | United Kingdom . |
| 1313093 | 4/1973 | United Kingdom . |
| 1349738 | 4/1974 | United Kingdom . |
| 2099157 | 12/1982 | United Kingdom . |

OTHER PUBLICATIONS

Jones et al., "A Rapid Accurate Unsteady-State Klinkenberg Permeameter", Oct. 1972, Society of Petroleum Engineers Journal, pp. 383-397.

Walls et al., "Effects of Pressure and Partial Water Saturation on Gas Permeability in Tight Sands: Experimental Results", Sep. 1980, Society of Petroleum Engineers Journal, pp. 1-11.

Freeman et al., "Low Permeability Laboratory Measurements by Nonsteady State and Conventional Methods", 1981, Society of Petroleum Engineers Journal, pp. 1-12.

Primary Examiner—Stewart J. Levy
Assistant Examiner—Hezron E. Williams
Attorney, Agent, or Firm—Lee C. Robinson, Jr.

[57] ABSTRACT

The permeability of a core sample is measured during nonsteady state flow of fluid therethrough. A predetermined test pressure is supplied to an upstream end of the core sample while that sample is disposed in a fixed, closed volume and is subjected to a constant, predetermined confining pressure. The change in pressure across the core sample, with the passage of time, is measured; and the permeability of the core sample is determined as a function of the time-related measure of pressure change.

20 Claims, 7 Drawing Figures

METHOD AND APPARATUS FOR NONSTEADY STATE TESTING OF PERMEABILITY

BACKGROUND OF THE INVENTION

This invention relates to a method and apparatus for measuring the permeability of a core sample and, more particularly, to such a method and apparatus whereby the permeability of the core sample is measured during nonsteady state flow conditions.

The permeability of a sample of material taken from a subterranean formation is an important measurement in evaluating the quantity and accessibility of petroleum deposits, natural gas formations, and the like that might be present in that subterranean formation. Permeability relates the volumetric flow rate of such petroleum or natural gas to a given pressure differential.

The unit of measure of permeability is expressed as a "Darcy", and the permeability of many subterranean reservoirs is expressed in units of "milli-darcies" (md) or "micro-darcies" ($\mu$d). As may be appreciated, it is far simpler to recover useful material, such as natural gas and other useful fluids, from subterranean formations having relatively higher permeability. However, new technology has encouraged serious consideration of fluid recovery from subterranean rocks having relatively "tight" or low permeability. Consequently, there is a need to measure the permeability of relatively "tight" core samples, wherein the expected permeability is in the micro-darcy range. However, conventional permeability-measuring techniques generally rely on the so-called "steady-state" method wherein a fluid, such as air, flows through a core sample under tests at steady-state conditions. Such steady-state techniques often are time-consuming and inefficient. In addition, if air is used to measure the permeability of the sample, the permeability which is determined is the permeability of that sample to air at a specific mean pore pressure, which may be substantially different from the permeability of that same sample to different gases at mean pressures where the mean free paths of the gas molecules are different, and may also be substantially different from the permeability to oil or other suitable liquid. Because of these errors, which are a function of the "testing" fluid and mean pressure that is used for the measurements, correction factors, known as Klinkenberg factors, are available by which the measured permeability can be "corrected" so as to reflect permeability of the sample to a gas at infinite mean pressure.

To reduce the time required to measure permeability of core samples well below the 45 minutes attending steady-state techniques, a nonsteady state test has been described by Stanley C. Jones in "A Rapid Accurate Unsteady-State Klinkenberg Permeameter", Journal S.P.E., October 1972. However, test runs made in accordance with the technique disclosed by Jones often require as much time as the steady-state technique, especially for samples having low permeability.

Another technique that has been proposed for improving the time required to measure low permeabilities is the so-called "pulse decay technique" described by Walls et al. in "Effects of Pressure and Partial Water Saturation on Gas Permeability in Tight Sands: Experimental Results", presented at the 55th Annual Fall Technical Conference and Exhibition of the Society of the Petroleum Engineers, September 1980. The drawback in the technique disclosed by Walls et al. appears to be the requirement for an undesirably long equilibrium time before a sample can be run.

Other investigations have been made for techniques which will provide rapid, accurate measurements of the permeability of core samples. As a result of such investigations, the method and apparatus disclosed herein were developed. In accordance with the present invention, a measure of the permeability of a core sample may be made in about one-tenth the time required by steady state methods.

OBJECTS OF THE INVENTION

Therefore, it is an object of the present invention to provide an improved method and apparatus for measuring the permeability of a core sample rapidly and accurately.

Another object of the present invention is to provide an improved nonsteady state method of measuring the permeability of a core sample, and to provide apparatus for carrying out that method.

A further object of this invention is to provide a technique for measuring the permeability of a core sample based upon pressure changes across that sample with the passage of time.

Various other objects, advantages and features of the present invention will become readily apparent from the ensuing detailed description, and the novel features will be particularly pointed out in the appended claims.

SUMMARY OF THE INVENTION

In accordance with the present invention, a method and apparatus are provided for measuring the permeability of a core sample. The core sample is disposed in a fixed, closed volume and is subjected to a constant, predetermined confining pressure. A predetermined test pressure, much less than the confining pressure, is applied to an upstream end of the core sample. The change in pressure across the core sample with the passage of time then is measured; and its permeability is determined as a function of the time-related measure of pressure change. In accordance with one aspect of the present invention, the change in pressure across the core sample is measured by sensing the change in pressure at the downstream end of the core sample.

According to one feature of this invention, time samples are obtained when the downstream pressure changes by a predetermined increment. The measured pressure changes and sampled times are combined with the measured length and cross-sectional area of the core sample, the initial, quiescent pressure at the downstream end, the viscosity of the fluid which is used to apply pressure to the upstream end, the closed volume into which the downstream end of the core sample exits and the porosity of the core sample.

Another feature of this invention is to detect when the downstream pressure reaches a predetermined proportion of the test pressure, and then to select a portion of the pressure measurements and time samples which had been obtained prior to the downstream pressure reaching the predetermined proportion; the permeability of the core sample being determined as a function of such selected pressure measurements and time samples.

In accordance with a still further feature of this invention, pressure and time samples are obtained whenever the downstream pressure changes by a predetermined increment. For example, samples are taken no matter how little time has passed from a preceding sample if the downstream pressure changes by more than +0.875 psig. Likewise, the downstream pressure must change by at least +0.05 psig before a sample is taken no matter how much time has passed from a preceding sample.

In a preferred embodiment, a suitably programmed computer carries out the following mathematical equation:

$$\frac{K_\infty A t}{V_D \mu L} + I = -C_2 P_L + (C_2 b - .5 C_1)\log(P_0^2 + 2bP_0 - P_L^2 - 2bP_L) - [C_2(P_0^2 + 2bP_0 + 2b^2) - (C_1 b + C_0)] \frac{\left[\tanh^{-1}\frac{(-P_L - b)}{(P_0 + b)}\right]}{(P_0 + b)}$$

where
$K_\infty$ = Klinkenberg permeability
$C_0, C_1, C_2$ = coefficients of $P_L$ from approximation of $F(P_L)$ which is a coefficient of flow that accounts for the overall effect of variable mass flow
$P_0$ = pressure at upstream end of sample
$P_L$ = pressure at downstream end of sample
$b$ = Klinkenberg slip (in atmospheres)
$A$ = cross-sectional area of core sample
$V_D$ = said closed volume
$\mu$ = viscosity of said fluid
$L$ = length of core sample
$t$ = time
$I$ = integration constant.

BRIEF DESCRIPTION OF THE DRAWINGS

The following detailed description, given by way of example, will best be understood in conjunction with the accompanying drawings in which.

DETAILED DESCRIPTION OF CERTAIN PREFERRED EMBODIMENTS

Figure 1:
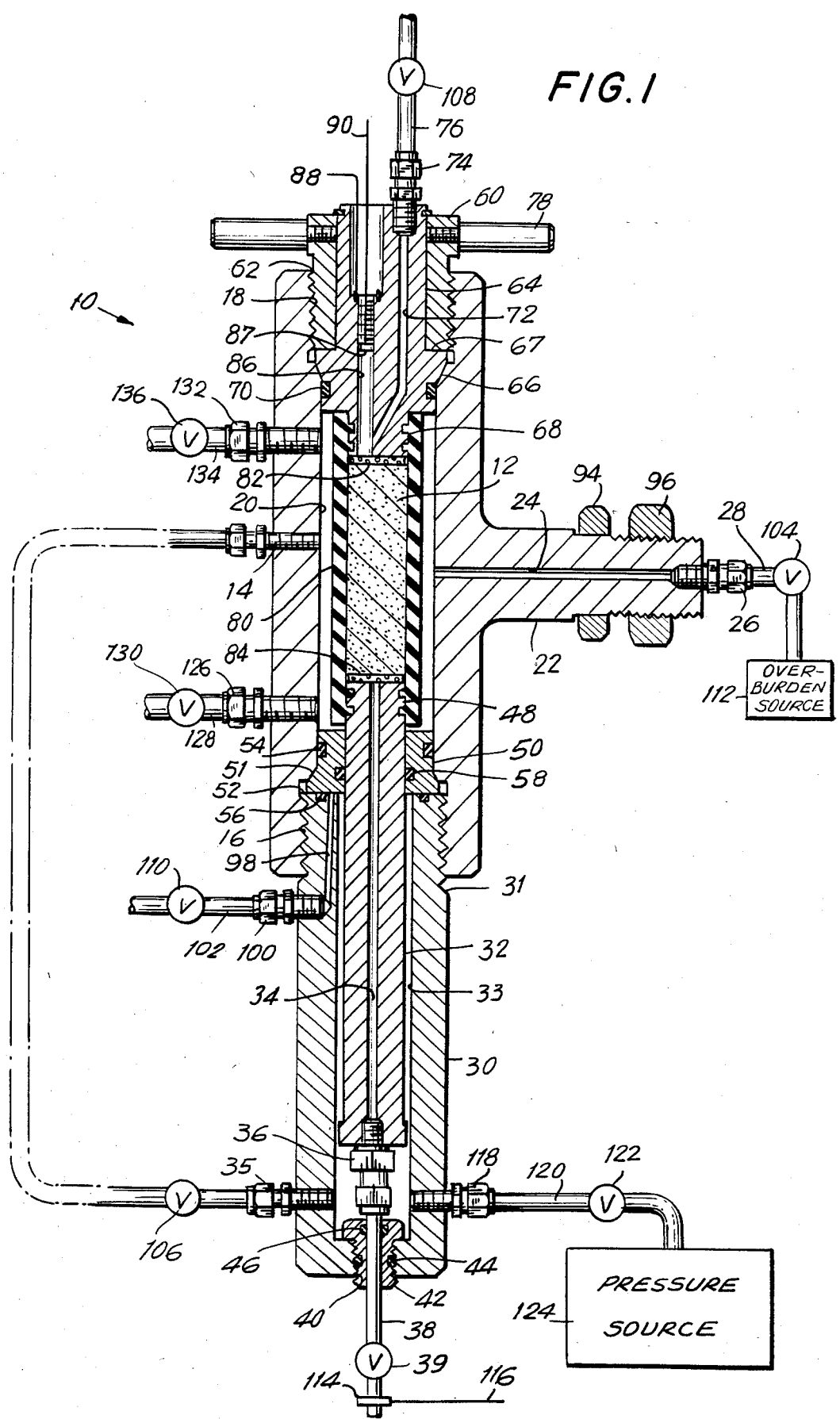
FIG. 1 is a sectional view of a preferred embodiment of a core holder which can be used to contain a core sample whose permeability is measured.

Referring now to the drawings, and in particular to FIG. 1, there is illustrated one embodiment of a core holder 10 which can be used with the present invention to measure the permeability of a core sample 12 that is derived from a subterranean formation.

Core holder 10 is comprised, principally, of a core holding body 14, a cap 30 disposed at one end thereof, and a cap 60 disposed at the opposite end thereof. Sample 12 is disposed within the core holding body, and is maintained between caps 30 and 60. Core holding body 14 is generally cylindrical and is hollow. Screw threads 16 are disposed at one end thereof, and are adapted to mate with screw threads 31 provided at one end of cap 30. Similar screw threads 18 are provided at the other end of core holding body 14, these latter screw threads being adapted to mate with screw threads 62 of cap 60. As shown in FIG. 1, and as will be described further below, when caps 30 and 60 are secured to opposite ends of core holding body 14, as when these caps are screwed into the opposite ends of the core holding body, an internal chamber 20 is defined by the interior wall of core holding body 14 and longitudinally spaced-apart sealing elements 50 and 66 which are confined by caps 30 and 60, respectively.

A pipe 22 is formed integrally with the side wall of core holding body 14, this pipe being provided with a channel 24 therein. In an alternative embodiment, suitable fittings are provided in the side wall of the core holding body to which pipe 22 is secured. Channel 24 communicates with internal chamber 20 and is provided, at its free end, with a fitting 26 whereby channel 24 is coupled to a high pressure tube 28. Channel 24 is adapted to supply suitably pressurized fluid to internal chamber 20.

Cap 30 is illustrated as being generally cylindrical and, as mentioned above, is provided with screw threads 31 at one end thereof, whereby cap 30 is screwed into a corresponding end of core holding body 14. Cap 30 is provided with a bore 33 in which is disposed a slidable plug 32. Bore 33 sometimes is referred to herein as a lower chamber. As will be described, an annular sealing element 50 cooperates with cap 30 and plug 32 to seal these latter elements to core holding body 14, and thereby separate internal chamber 20 from lower chamber 33.

Plug 32 is provided with a channel 34 therein, this channel communicating with sample 12. A fitting 36 is adapted to be coupled to a smooth stiff wall tube 38, this fitting communicating with channel 34 so as to provide a fluid passageway from tube 38 to this channel. A suitable valve 39, which is operative to supply a fluid at a constant, predetermined pressure to channel 34, as will be described, is coupled to tube 38. As illustrated, this tube passes through an opening 40 at the end of cap 30 remote from chamber 20. Opening 40 is sealed from ambient and, to this effect, a stopper 42 is disposed therewithin, this stopper including O-rings 44 and 46 by which fluid seals are provided between the stopper and cap 30, and also between the stopper and tube 38. In this manner, lower chamber 33, that is, the chamber in which plug 32 is disposed, is sealed from ambient.

Also shown in FIG. 1 is a pressure indicator 114, disposed in the fluid path upstream of valve 39 and sample 12, for example, disposed in tube 38, which may be of conventional construction. The pressure indicator is adapted to produce electrical pressure signals representing the pressure supplied by valve 39 to the sample, which signals are coupled to electrical circuitry (to be described) by electrical conductors 116. A suitable source of test pressure (not shown) is coupled to valve 39 to be supplied to the sample when the valve opens. This valve may be electrically controlled so as to open in response to a suitable command signal supplied thereto.

As alluded to above, an annular sealing element 50 separates chamber 20 from lower chamber 33. This annular sealing element surrounds upper end 48 of plug 32 and seats upon upper end 52 of cap 30. In one embodiment, O-rings 54, 56 and 58 are provided to effect fluid seals between sealing element 50, on the one hand, and the interior wall of core holding body 14, cap 30 and plug 32, respectively. Thus, internal chamber 20 is sealed from lower chamber 33. In an alternative embodiment, O-ring 58 may be omitted, whereby chambers 20 and 33 may be in fluid communication with each other. It will be seen that, with the omission of O-ring 58, core holder 10 may be viewed as an hydrostatic cell. When O-ring 58 is used, the core holder may be viewed as a triaxial cell. As a further alternative (shown in broken lines), chambers 20 and 33 may be connected by an external tube containing a valve therein which, in its open condition, connects the chambers and, in its closed condition, separates these chambers.

It may be appreciated that, to assemble the illustrated core holder, plug 32 is disposed within lower chamber 33 of cap 30, and annular sealing element 50 is positioned about the plug, and seated upon upper end 52 of the cap. Then, the cap is screwed into the corresponding end of core holding body 14. For proper positioning of the plug and annular sealing element, the outer wall of the sealing element is provided with an inclined portion 51 which is urged against a corresponding inclined portion of the interior wall of the core holding body.

Cap 60, disposed at the opposite end of core holding body 14, is provided with screw threads 62, as mentioned above, to enable this cap to be screwed into the corresponding end of the core holding body. In the illustrated embodiment, cap 60 is provided with a bore which receives a plug 64. In an alternative embodiment, the plug and cap are of integral, one-piece construction. It will, therefore, be understood that references to cap 60 and plug 64, as used in the present description, are also intended to refer to such an integral, one-piece cap.

Plug 64, or the equivalent portion of a one-piece cap, is provided with a projection 66 at one end thereof, this projection terminating in an extension 68, the latter extending into chamber 20. It is seen that the geometric configuration of projection 66 and extension 68 is substantially identical to the geometric configuration of annular sealing element 50 and upper end 48 of plug 32. Projection 66 is provided with an O-ring 70 so as to provide a fluid seal with the interior wall of core holding body 14. As shown, projection 66 serves to define one end of chamber 20.

Plug 64 is provided with a channel 72 to which a fitting 74 is coupled. A tube 76 and valve 108 are adapted to be secured to fitting 74 to supply, contain or drain pressurized fluid to, in or from channel 72.

Projection 66 includes an annular flange 67 against which the free end of cap 60 is urged. Hence, when cap 60 is screwed into its corresponding end of core holding body 14, plug 64 is driven into sealed relationship with the interior wall of core holding body 14. As was described previously with respect to annular sealing element 50, the wall of projection 66 of plug 64 includes an inclined portion which is urged against a complementary incline of the interior wall of the core holding body.

The upper end of cap 60, as illustrated in FIG. 1, includes a handle 78 to effect the securing of this cap to the core holding body.

A flexible sleeve 80 is provided to receive core sample 12. In one embodiment, flexible sleeve 80 is comprised of a resiliently flexible material, such as rubber or plastic, adapted to retain the core sample. For example, the flexible sleeve may be formed as a laminate of suitable plastic materials, the inner layer which is in contact with sample 12 being of relatively soft plastic material, and the outer-most layer being of relatively harder plastic material. In one embodiment to be described, flexible sleeve 80 is gas permeable, but is practically impervious to various liquids, such as water. In an alternative embodiment, the flexible sleeve is practically gas-impermeable. Advantageously, flexible sleeve 80 may be heat shrinkable.

A pair of permeable members 82 and 84 are disposed at opposite ends of core sample 12 and, as illustrated in FIG. 1, are positioned with the core sample within flexible sleeve 80. The permeable members function as filter elements and may be porous sintered steel or the like. Thus, permeable members 82 and 84, together with flexible sleeve 80 confine core sample 12. It is seen that permeable member 82 is in fluid communication with channels 72 and 86, both channels being provided in plug 64. Likewise, permeable member 84 is provided in fluid communication with channel 34 which, in turn, is provided within plug 32. Consequently, pressurized test fluid may be supplied from a suitable source, through tube 38, fitting 36 and channel 34 to permeable member 84, this fluid exiting from core sample 12 via permeable member 82, channel 72, fitting 74 and tube 76. If desired, fluid may be supplied to core sample 12 in the opposite direction. For convenience, that end of the core sample to which the fluid is supplied is referred to as the upstream end, and that end of the sample from which this fluid exits is referred to as the downstream end. Plugs 32 and 64 are in contact, preferably fluid-sealed contact, with permeable members 84 and 82, respectively. As will become apparent, this facilitates the supply of pressurized test fluid to sample 12 retained within flexible sleeve 80.

In the illustrated embodiment, channel 86 is in fluid communication with sample 12 via permeable member 82 and is sealed to ambient by valve 108. A suitable pressure transducer 87, which may be of conventional construction, is disposed by self-contained threads within channel 86, and is adapted to provide an electrical signal indicative of the fluid pressure within channel 86. An "O" ring 88 on the upper end of transducer 87 seats against a shoulder at the top of channel 86 (as viewed in FIG. 1) to seal the channel from ambient. Electrical leads 90 (only one of which being shown) extend from the transducer to electrically connect it with other circuitry, shown in FIG. 2 for example, for the purpose of utilizing the electrical pressure signals produced by the transducer to determine the permeability of sample 12. Electrical leads 90 also may supply operating potential to pressure transducer 87 from a suitable power supply.

The combination of channel 86, "O" ring 88, channel 72 and tube 76 (the latter being selectively closed, or sealed, by a valve 108) defines a fixed, closed volume. Preferably, this closed volume is in the range of one to four times the pore volume of sample 12, whose downstream end exits into this closed volume. This relationship is readily attained, since the length, cross-sectional area and material constituting the sample generally are sufficiently known. If desired, channels of different volume, or a channel of adjustable volume, may be substituted for tube 76.

Preferably, upper end 48 of plug 32, and also extension 68 of plug 64, are provided with suitable corrugations, ridges, and increased diameters to seal opposite ends of flexible sleeve 80. Additional retaining members (not shown) may be provided for this purpose, if need be.

Pipe 22 is provided with a washer 94 and a nut 96 advantageously to couple the pipe to additional apparatus (not shown). This combination of washer and nut may be omitted, if desired.

Lower chamber 33, within which plug 32 is disposed, is coupled to a venting channel 98. This venting channel advantageously permits liquid, which is introduced into lower chamber 33 during a test run to be degassed. Venting channel 98 is coupled to a suitable fitting 100 to which a tube 102 is secured.

Various valves are coupled to the illustrated fittings for the purpose of selectively controlling the entrance and exhaust of fluid to and from the various channels. For example, a valve 104 is coupled to tube 28 to selectively supply fluid under relatively high pressures to channel 24. This fluid serves to subject chamber 20 to a correspondingly high pressure, and thus apply a confining pressure to core sample 12. The pressure supplied to tube 28 is derived from a source 112 and is adapted to simulate the high pressures which are present in the subterranean formation from which sample 12 is derived. Such high subterranean pressures typically are referred to as "overburden" pressures and, consistent with this nomenclature, source 112 is referred to as an overburden source adapted to supply overburden (confining) pressures to chamber 20. Similarly, a valve 110 is coupled to fitting 100 and is adapted to drain liquid from lower chamber 33 following a test run. As mentioned above, valve 108 is coupled to tube 76 and is adapted to supply, contain or drain, pressurized test fluid, such as air, through channel 72 to, or from, sample 12.

Valve 110, coupled to hose 102, is adapted to vent channel 98, and thus allow lower chamber 33 to be depleted of air as it is filled with, for example, water. Such venting serves to enable lower chamber 33 to be pressurized with a suitable degassed liquid, such as water.

In addition to the aforedescribed fittings and valves, FIG. 1 illustrates a fitting 118 adapted to connect a tube 120 directly to lower chamber 33. A valve 122 is coupled to tube 120, and is adapted to supply pressurized fluid from a suitable source 124 to the lower chamber. This source may be an overburden pressure source. Sources 112 and 124 may comprise a common source, with valves 104 and 122 being effective to determine the respective pressures which are supplied to chambers 20 and 33, respectively. Alternatively, the respective overburden sources may comprise separate sources of overburden pressure.

In FIG. 1, chamber 20 also is illustrated as being coupled via a fitting 126 and tube 128 to a valve 130. The purpose of this combination is to function either as a drain for pressurized liquid supplied to chamber 20 after the completion of a test run or, depending upon the orientation of the core holder, to supply suitable overburden pressurized fluid to chamber 20. Likewise, chamber 20 is coupled to a fitting 132, tube 134 and valve 136, this combination serving a similar alternative function as aforedescribed fitting 126, tube 128 and valve 130. It will be appreciated that, depending upon the particular orientation or alignment of core holder 10, the overburden pressurized fluid may be supplied to chamber 20 via fittings 126 and/or 132, and fitting 26, tube 28 and valve 104 may serve as a liquid drain. For example, if the illustrated core holder is rotated clockwise by 90°, channel 24 may function as a suitable drain channel for draining liquid from chamber 20, following the completion of a test run.

Briefly, when the nonsteady state permeability test of sample 12 is carried out, a suitable overburden (or confining) pressure of up to (and preferably not in excess of) 15,000 psi is supplied to chamber 20 from, for example, source 112. The confining pressure must be sufficient to prevent bypassing of air around the sample. It also has been found that the measured permeability of a sample is affected by the magnitude of the effective overburden pressure, particularly when measuring microdarcy permeability samples. "Effective overburden pressure" is equal to the overburden pressure less the pore pressure. It is preferred, therefore, to apply effective overburden pressures that simulate reservoir conditions. A pressurized fluid, such as air, having a pressure on the order of about 100 psi, is coupled to tube 38 via valve 39. Valve 39 is opened to increase the upstream pressure supplied to sample 12 abruptly; and the pressure change at the downstream end of sample 12 is sensed by means of pressure transducer 87. The pressure in channel 86, which is included as part of the closed volume to which the downstream end of sample 12 exits, represents the increase in downstream pressure in response to the application of the 100 psi pressure to the upstream end of sample 12.

Changes in the downstream pressure with the passage of time are detected. For example, a time measurement may be made, as by sampling a suitable clock generator, each time the downstream pressure increases by 0.05 psi. Such time measurements, and concurrent pressure measurements, desirably are constrained to occur no greater than one measurement every 0.05 psi pressure increase, nor less than one measurement every 0.875 psi pressure increase. When the downstream pressure has been increased to approximately 90% of the upstream pressure (e. g. 90 psi) after a minimum of thirty measurements have been taken, and the elapsed time is greater than 600 seconds, or after a total of 100 measurements have been taken (regardless of the actual downstream pressure), the resultant pressure-time data are used to calculate permeability in accordance with the flow correction equation described below.

Figure 2:
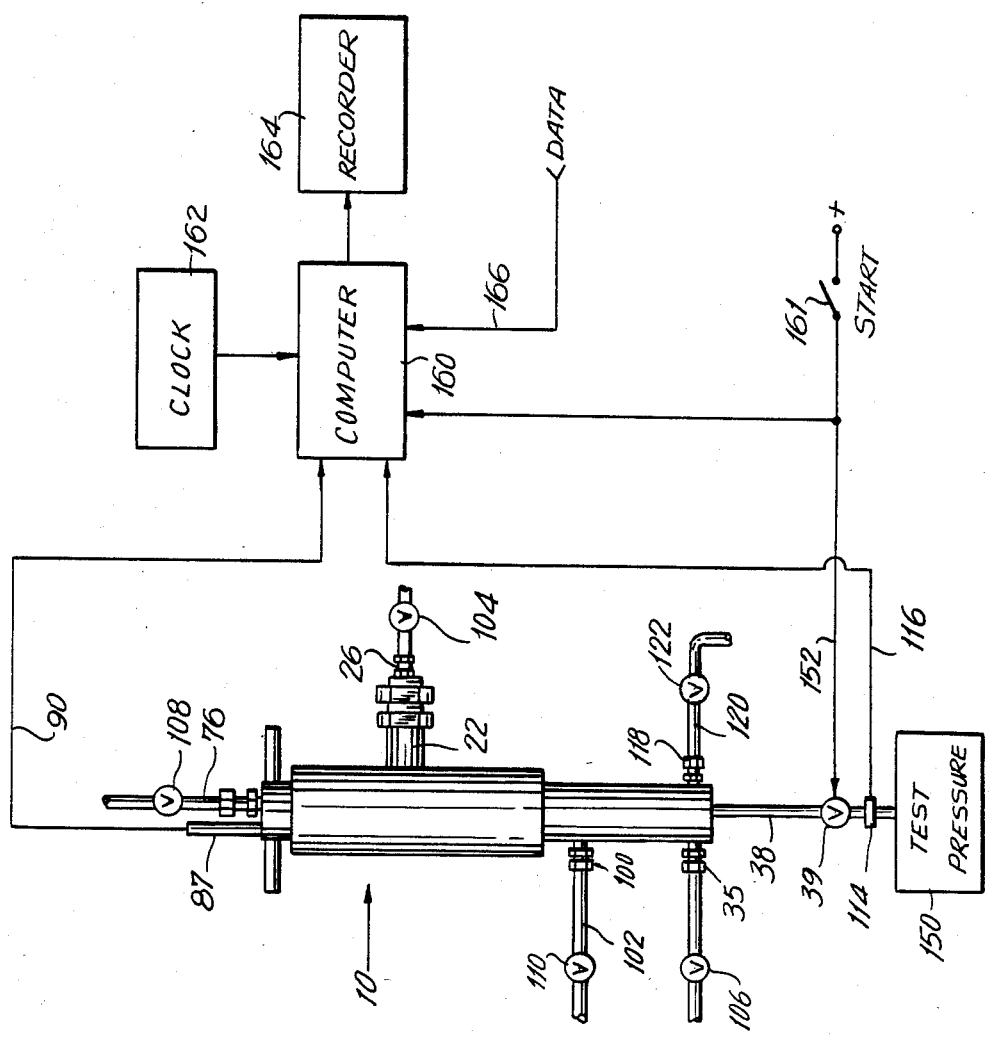
FIG. 2 is a block diagram of one embodiment of apparatus which can be used to measure the permeability of the core sample.

The aforedescribed technique for obtaining pressure and time measurements is carried out by the electrical system schematically represented by the block diagram shown in FIG. 2. Core holder 10 is seen to be the same core holder as described hereinabove with respect to FIG. 1. Accordingly, in the interest of brevity, further description of the core holder shown in FIG. 2 is not provided. It will be assumed, for the purpose of the present description, that valve 104 serves to couple suitable overburden pressure to the core sample disposed in core holder 10 via pipe 22. This overburden pressure applies a predetermined, constant confining pressure to the core sample within the pressure range described previously.

It is further assumed that tube 38 supplies fluid, such as air, having a predetermined, constant test pressure on the order of about 100 psi to the upstream end of the core sample. As illustrated in FIG. 2, a suitable source 150 of test pressure fluid is coupled to valve 39 which, when opened, applies this test pressure to the upstream end of the core sample. Of course, during the permeability test, valve 108 is closed such that the downstream end of the core sample exits to a fixed, closed volume defined by channel 72, that portion of tube 76 upstream of valve 108, and channel 86, all as discussed above.

Leads 90 electrically couple pressure transducer 87, which is adapted to measure the downstream pressure of the core sample, to a suitably programmed computer 160. Likewise, leads 116 serve to electrically couple pressure indicator 114, which is adapted to measure the test pressure applied to the upstream end of the core sample, to computer 160.

A suitable clock generator 162, known to those of ordinary skill in the art, is coupled to the computer and is adapted to supply time signals thereto which, when measured, or sampled, provide suitable indications of the passage of time. Computer 160 also is coupled to a "start" switch 161 which, when actuated (e. g. opened), initiates the operation of the computer to carry out the permeability test, as will be described. Start switch 161 is a pressure actuated switch coupled, via leads 152, to valve 39 and opens in response to a pressure greater than 10 psig provided at the valve. It may be appreciated, therefore, that the start switch is a suitable pressure actuated valve/switch of a type that is commercially available.

The computer also is coupled, via leads 166, to a data entry source, such a conventional keyboard, or the like, to be supplied with data representing various parameters relating to the core sample under test. For example, data representing the length L and cross-sectional area A of the core sample are supplied to computer 160. In addition, data representing the closed volume $V_D$ into which the downstream end of the core sample exits also is supplied, as is data representing the viscosity $\mu$ of the pressurized test fluid supplied to the core sample. The foregoing is intended to be merely illustrative of data supplied to computer 160 and is not intended to be all-inclusive thereof.

Optionally, computer 160 also is coupled to a suitable recording device 164 such that the permeability of the tested core sample, as measured and determined by the computer, may be recorded. Alternatively, computer 160 may supply samples of the determined permeability of the core sample, over a period of time, which samples may be recorded and graphically plotted by the recording device.

In operation, valve 108 initially is opened such that the pressure at the downstream end of the core sample is made equal to ambient pressure, and this valve remains open while containing pressure is applied and the sample reaches equilibrium. Then, valve 108 is closed. Initially, a quiescent, initial downstream pressure $P_0$ is present in the closed volume to which the core sample exits. This quiescent downstream pressure $P_0$ is sensed by pressure transducer 87, and a corresponding electrical pressure signal representing this initial, quiescent downstream pressure $P_0$ is produced.

Valve 104 is opened so as to supply a suitable constant, predetermined confining pressure to the core sample. As mentioned above, the effective confining pressure should simulate reservoir conditions.

Prior to actuating start switch 161, an operator enters into computer 160 data representing the length L of the core sample, the cross-sectional area A thereof, its porosity, the closed volume $V_D$, the type of test fluid that is used (e. g. air or nitrogen), the viscosity $\mu$ of the pressurized test fluid to be supplied to the core sample, and the room, or ambient, temperature. Then, valve 39 is opened to actuate start switch 161 and initiate the operation of computer 160 to carry out the test run. Valve 39, when opened, supplies fluid, such as air, from source 150 to the upstream end of the core sample. This fluid is supplied with a constant test pressure which, as mentioned above, is on the order of about 100 psi. This pressure is sensed by pressure indicator 114 to supply a corresponding electrical pressure signal to computer 160 representing this constant test pressure.

Figure 3:
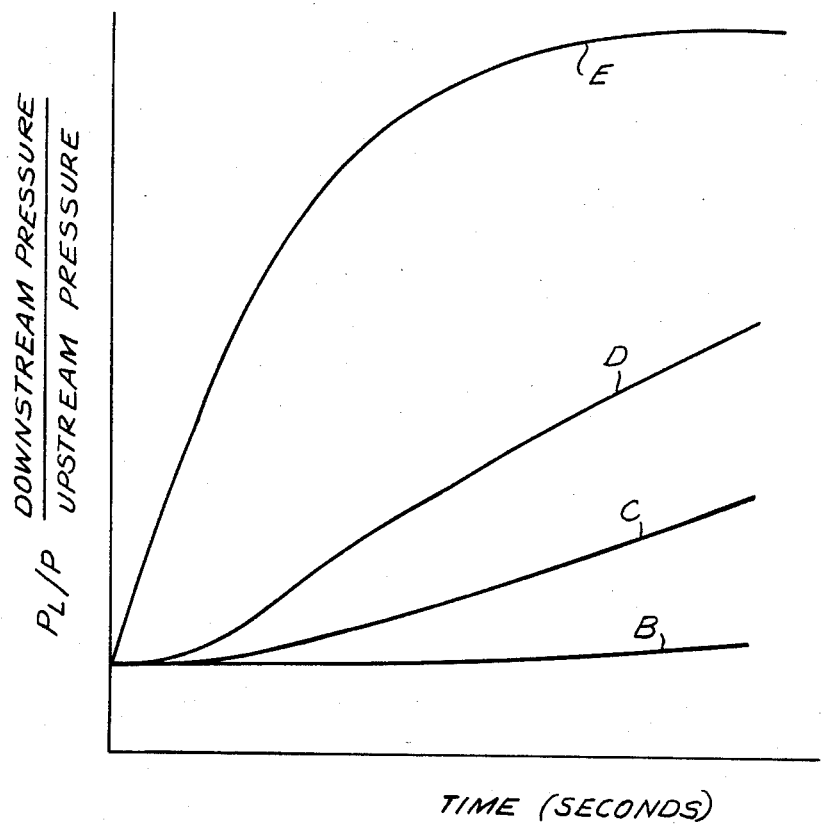
FIG. 3 is a graphical representation of pressure profiles for core samples having different permeabilities.

It is appreciated that, since the initial, quiescent downstream pressure $P_0$ was equal to ambient, the test pressure supplied to the upstream end of the core sample will result in a gradual increase in the pressure at the downstream end thereof. Of course, the rate at which the downstream pressure increases is a function of the permeability of the confined sample. FIG. 3 graphically represents the "pressure profiles" of four core samples having respectively different permeabilities. These pressure profile characteristic curves represent the change in the downstream pressure $P_L$ with respect to time when valve 39 is opened to supply the test pressure P to the upstream end of the core sample. Hence, in FIG. 3, the abscissa represents time, in terms of seconds, and the ordinate represents the ratio of the downstream pressure to the upstream pressure ($P_L/P$).

Curve B represents a very slow increase in downstream pressure $P_L$. The permeability $K_\infty$ of sample "B" is about 1.5 micro-darcies ($\mu$d); and the Klinkenberg correction factor "b" for this sample is about 6.4 atmospheres. Curve C represents a greater increase in downstream pressure $P_L$ for sample "C" having permeability $K_\infty$ of about 11.5 $\mu$d and correction factor b of about 2.74. Curve D represents a still greater rate at which the downstream pressure $P_L$ increases for sample "D" having permeability $K_\infty$ of about 29.6 $\mu$d and correction factor b of about 1.84. Finally, curve E represents the fastest increase in downstream pressure $P_L$ for sample "E" having permeability $K_\infty$ of about 122.1 $\mu$d and correction factor b of about 1.25.

Thus, it is seen that, depending upon the permeability of the core sample, the downstream pressure $P_L$ thereof increases at a rate which is a function of its permeability $K_\infty$.

Figure 4A:
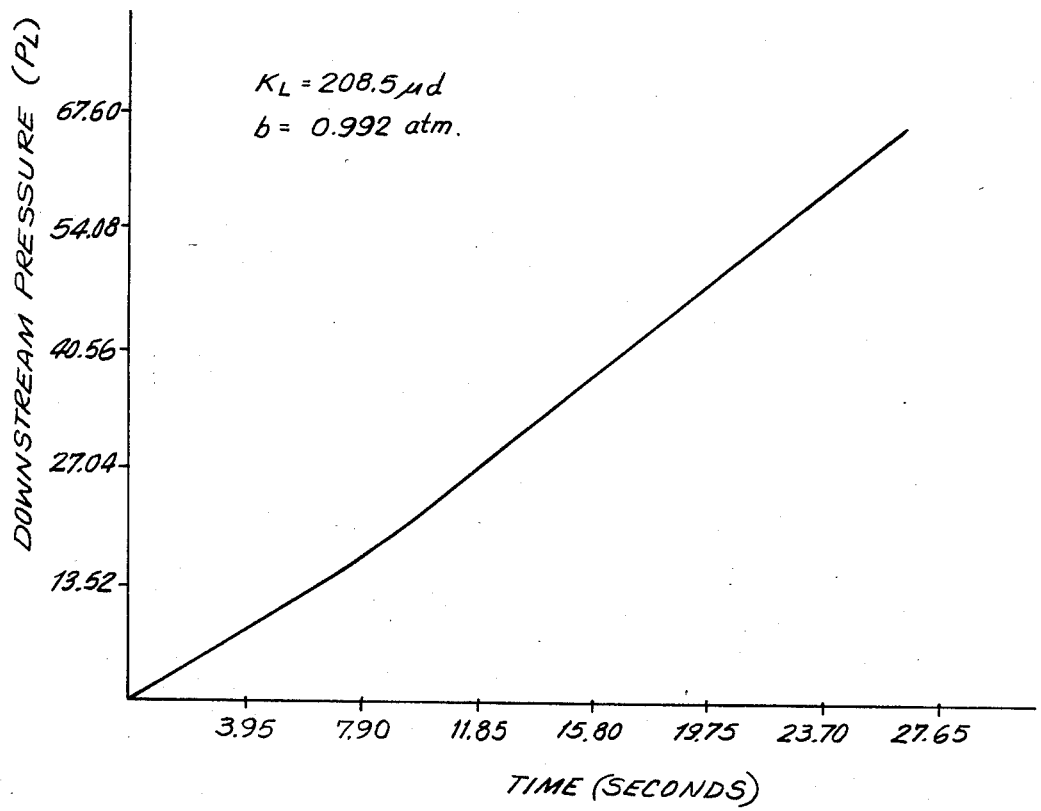
FIGS. 4A and 4B represent the pressure profiles of two core samples having widely different permeabilities.

Assuming that the pressure of the test fluid supplied to the upstream end of the core sample remains constant at 100 psi, then, for a core sample having permeability $K_\infty$ of about 208.5 $\mu$d and a correction factor b of about 0.992 atmospheres, FIG. 4A represents the increase of downstream pressure $P_L$ with respect to time. This downstream pressure reaches a level of about 50 psi, or about one-half the test pressure, in about 20 seconds. If the permeability of the core sample is about 29.6 $\mu$d, such as represented by curve D in FIG. 3, then the relationship between the downstream pressure $P_L$ and time is of the type graphically depicted in FIG. 4B. Here, with this low permeability, that is, with a "tight" sample, the downstream pressure is about 1 psi after about 20 seconds.

Figure 4B:
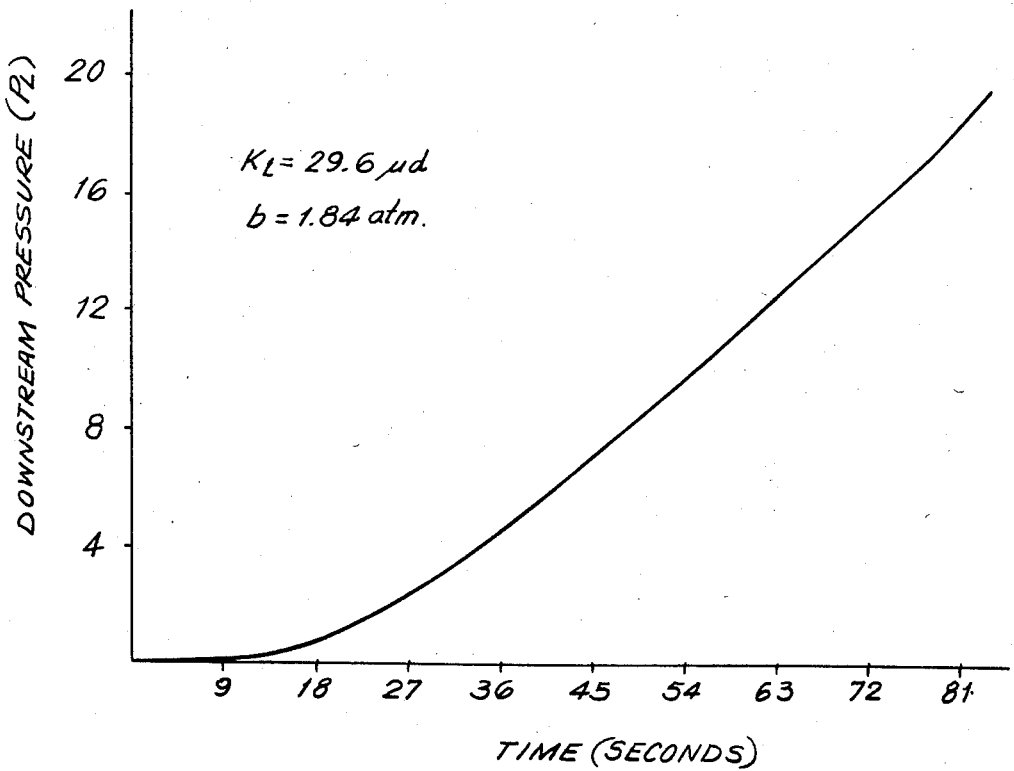

The slope of the pressure profile obtained from supplying the pressurized test fluid to the core sample, that is, the slope of the curves illustrated in FIGS. 3 and 4A, 4B, may be represented as $P'_L$, where $$P_L' = \frac{dP_L}{dt}$$

If X is any point along the length of the core sample, then $g = x/L$. The volumetric flow rate g at any point x along the length of the core sample may be expressed as:

$$q(g,t) = \frac{V_D P_L'[1 + \delta f(c,g)]}{P(g,t)} \quad (1)$$

$t$ = time $V_D$ = the closed volume into which the downstream end of the core sample exists $\delta$ is a function of the length, cross-sectional area and porosity (which can be measured) of the core sample, as well as the closed volume and the correction factor b $f(c,g)$ is a function of the downstream pressure $P_L$, the correction factor b and the location of point x $P(g,t)$ = the change in pressure with respect to time at the point x.

If the factor $f(c,g)$ is integrated over the range from $g=0$ to $g=1$, the integrated function may be expressed as $G(c)$. Based upon Darcy's equation, the continuity equation for one dimension, the ideal gas law and correcting for non-constant mass flow, the following may be derived from equation (1):

$$\frac{-2V_D \mu L P_L'}{K_\infty A}[1 + \delta G(c)] = P_L^2 + 2bP_L - (P_0^2 + 2bP_0) \quad (2)$$

Figure 5:
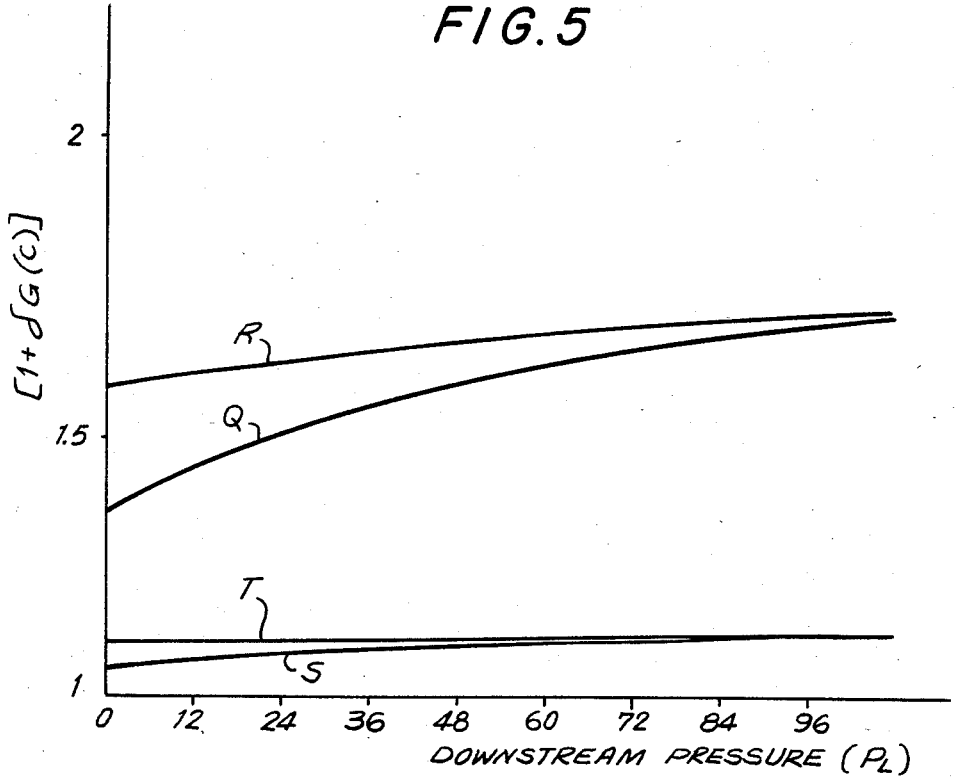
FIG. 5 is a graphical representation of the characteristics of different core samples which are helpful in understanding the operation of the present invention.

The factor $[1+\delta G(c)]$ varies with downstream pressure $P_L$ as a function of the porosity $\phi$ and correction factor b of the sample. FIG. 5 represents typical characteristic curves of this relationship for samples "Q", "R", "S" and "T", where sample "Q" has a porosity of about 0.3 and a correction factor of about 1, sample "R" has a porosity of about 0.3 and a correction factor of about 7, sample "S" has a porosity of about 0.05 and a correction factor of about 1, and sample "T" has a porosity of about 0.05 and a correction factor of about 7. Assuming that the test pressure is 100 psi, it is seen that all of the curves exhibit a substantially linear relationship when the downstream pressure reaches about 45 psi. Thus, if equation (2) is used to determine permeability $K_L$, the solution to this equation is simplified if the downstream pressure measurements are utilized for those regions wherein the factor $[1+\delta G(c)]$ can be represented as a quadratic function of $P_L$. Accordingly, for this region, the following expression is a good approximation:

$$[1+\delta G(c)] = C_0 + C_1 P_L + C_2 P_L^2 \quad (3)$$

where $C_0$, $C_1$ and $C_2$ are constants determined by the "least squares best fit" criteria.

When equation (3) is substituted into equation (2), and the slope $P'_L$ of the downstream pressure profile is integrated from time $t_1$ when the downstream pressure is equal to $P_1$ to time $t_2$ when the downstream pressure is equal to $P_2$, a mathematical representation of permeability $K_\infty$ based upon such downstream pressure and time measurements may be expressed as:

$$\frac{K_\infty A t}{V_D \mu L} + I = -C_2 P_L + (C_2 b - .5C_1)\log(P_0^2 + 2bP_0 - P_L^2 - 2bP_L) - [C_2(P_0^2 + 2bP_0 + 2b^2) - (C_1 b + C_0)] \frac{\left[\tanh^{-1}\frac{(-P_L - b)}{(P_0 + b)}\right]}{(P_0 + b)} \quad (4)$$

where $K_\infty$ = Klinkenberg permeability $C_0, C_1, C_2$ = coefficients of $P_L$ from approximation of $F(P_L)$ which is a coefficient of flow that accounts for the overall effect of variable mass flow $P_0$ = pressure at upstream end of sample $P_L$ = pressure at downstream end of sample b = Klinkenberg slip (in atmospheres)

A = cross-sectional area of core sample $V_D$ = the closed volume $\mu$ = viscosity of the fluid L = length of the core sample t = time I = integration constant.

Computer 160 may be suitably programmed so as to implement equation (4). It is appreciated that the operator enters into the computer all of the data necessary for equation (4) except for the factors $P_0$, $P_L$ and t. These factors, however, are supplied to computer 160 by pressure indicator 114, pressure transducer 87 and clock generator 162. The manner in which the computer processes the pressure and time signals supplied thereto now will be described.

The pressure signals supplied to computer 160 are sensed, or measured, and when it is determined that the downstream pressure changes by a predetermined increment $\Delta P$, the time signal is sampled. As a numerical example, when the downstream pressure increases by 0.05 psi, the time signal is sampled. Accordingly, time samples are obtained for each incremental change $\Delta P$ in the downstream pressure. Thus, for each incremental change in the downstream pressure, a measurement of $P_2$ is obtained, as well as a measure of time since the start of measurement. Hence, incremental determinations of the permeability are made. Computer 160 may use this data to produce a measure of the permeability.

When the downstream pressure reaches a predetermined proportion of the test pressure, for example, when the downstream pressure is about 90% of the test pressure, the permeability determination is made. However, permeability is not determined unless a minimum of thirty time/pressure samples have been obtained. If, after 100 such samples have been taken, the downstream pressure has not yet reached the predetermined proportion of the test pressure, then permeability is determined on the basis of the 100 samples which have been obtained.

Figure 6:
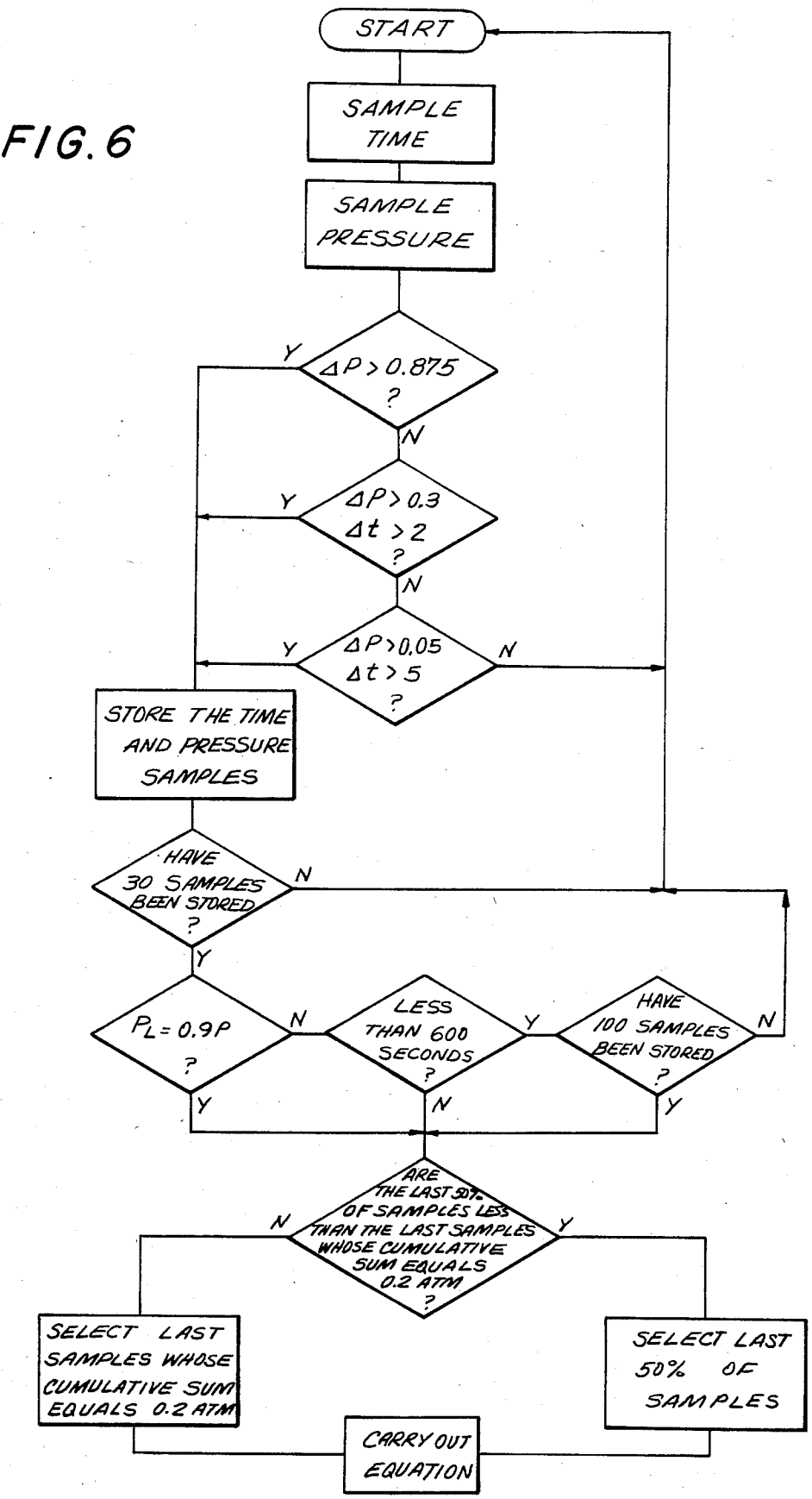
FIG. 6 is a flow chart representing the operation of a suitably programmed computer which can be used to carry out the present invention.

A flow chart representing the manner in which time/pressure samples are obtained for carrying out equation (4) is illustrated in FIG. 6. This flow chart is a diagrammatic representation of a suitable program, or subroutine, for computer 160 in order to obtain the necessary samples. The illustrated flow chart commences with the START condition in response to, for example, the closing of start switch 161 (FIG. 2). It is recalled that, when valve 39 is opened, test fluid, having constant, predetermined test pressure, is supplied to the core sample and start switch 161 is actuated. This test pressure, also referred to herein as the upstream pressure, is sensed by pressure indicator 114 to supply a corresponding pressure signal to computer 160.

Once start switch 161 has been actuated, the illustrated routine advances to sample the time signal produced by clock generator 162. As may be appreciated, this clock generator may be of the type which generates a series of clock pulses at a predetermined, fixed rate. Thus, each time this time signal is sampled, an indication of the passage of a small increment of time is provided. In addition to sampling the time signal, the pressure signal produced by pressure transducer 87 is sampled. Then, inquiry is made as to whether the downstream pressure, as represented by the pressure signal produced by transducer 87, has changed by more than the increment $\Delta P > 0.875$ psi. If this inquiry is answered in the negative, the routine advances to inquire if the downstream pressure has changed by more than 0.3 psi ($\Delta P > 0.3$) and if more than two seconds have elapsed ($\Delta t > 2$). If not, the further inquiry is made as to whether the downstream pressure has changed by more than 0.05 psi ($\Delta P > 0.05$) and whether more than five seconds have elapsed ($\Delta t > 5$). If this last inquiry also is answered in the negative, the routine will return to its START condition. If any of the aforementioned inquiries is answered in the affirmative, the samples of the time and pressure signals are stored in, for example, a suitable storage location in computer 160.

After each time/pressure sample is stored, inquiry is made as to whether a total of thirty such samples have been stored. If this inquiry is answered in the negative, the routine returns to its START condition; and the foregoing operations are repeated. However, once thirty time/pressure samples have been stored, inquiry next is made as to whether 600 seconds have elapsed since the start of the test or whether the downstream pressure $P_L$ has reached a predetermined portion of the upstream pressure, that is, whether the downstream pressure is equal to 90% of the test pressure. If less than 600 seconds have passed and the downstream pressure is not equal to 90% of the test pressure, inquiry next is made as to whether 100 time/pressure samples have been stored. If not, that is, if more than thirty but less than 100 samples have been stored, but the downstream pressure has not yet reached 90% of the test pressure and the elapsed time is less than 600 seconds, the illustrated routine returns to its START condition; and the foregoing operations are repeated.

If, however, the downstream pressure has reached 90% of the test pressure, or 600 seconds have elapsed, or 100 time/pressure samples have been stored, the illustrated routine advances by either one of two selectable paths. The selection of the path which is followed is a function of the inquiry of whether the last 50% of those samples which have been stored is less than those stored pressure samples whose cumulative sum is equal to a pressure change of 0.2 atmospheres. If this inquiry is answered in the affirmative, the last 50% of those samples which have been stored are selected and used by the computer to implement equation (4). If this inquiry is answered in the negative, those stored pressure samples are selected whose cumulative sum is equal to a pressure change of 0.2 atmosphere. Of course, the corresponding time samples that have been taken with the pressure samples also are selected and utilized by computer 160 in implementing equation (4).

The initial downstream pressure $P_0$ may correspond to the pressure represented by the pressure signal produced by transducer 87 at the time that start switch 161 is activated. Alternatively, if this pressure is accurately known by the operator, data representing the initial downstream pressure $P_0$ may be entered via, for example, the manually operable keyboard mentioned hereinabove.

It should be appreciated that other equivalent arrangements may be used in commencing the routine represented by the flow chart shown in FIG. 6. For example, start switch 161 may initiate the operation of the routine illustrated in FIG. 6; whereupon computer 160 when supplies an actuating signal to open valve 39.

While the present invention has been particularly shown and described with reference to a preferred embodiment thereof, various changes and modifications in form and details may be made without departing from the spirit and scope of the invention. For example, the fluid which is utilized to supply the fixed, predetermined confining pressure to the core sample may comprise a suitable gas or, if desired, a liquid may be used. Although the test pressure has been described as being on the order of about 100 psi, other pressures may be used, as desired. Still further, although the flow chart shown in FIG. 6 operates to sense an incremental change in the downstream pressure P on the order of 0.05 psi, other incremental changes may be sensed, if desired. Likewise, the total number of stored samples from which a selection is made to implement equation (4) need not be limited solely between the aforedescribed range of 30 and 100 samples. Likewise, the predetermined proportion to which the downstream pressure increases can be other than 90% of the test pressure. In similar manner, the number of stored samples which are selected to implement equation (4) may be any desired number other than the last 50% of the stored samples.

Still further, although a preferred embodiment has been described as utilizing a computer 160, it may be appreciated that an electronic circuit, formed of discrete components, which circuit may be either a digital circuit or an analog circuit, may be used in accordance with the present invention to process the time and pressure signals so as to determine the permeability of the core sample.

It is, therefore, intended that the appended claims be interpreted as including the foregoing as well as other such changes and modifications.

What is claimed is:

1. A method of measuring the permeability of a core sample, comprising the steps of applying a fluid of predetermined test pressure to an upstream end of the core sample while the downstream end of said core sample exits to a closed volume that is approximately 1 to 4 times the pore volume of said core sample and while a predetermined constant confining pressure is applied to said core sample; measuring the change in the pressure at the downstream end of said core sample; measuring the time required for said pressure at said downstream end to change by a predetermined increment; and determining said permeability of said core sample as a function of said measured pressure changes and said measured times.

2. The method of claim 1 wherein said confining pressure does not exceed about 15,000 psi.

3. The method of claim 1 wherein said predetermined test pressure is approximately 100 psi.

4. The method of claim 1, further comprising the steps of measuring the length and cross-sectional area of said core sample, and measuring the initial pressure at said downstream end prior to the application of said fluid to said upstream end; and wherein said step of determining said permeability is an additional function of said measured length, cross-sectional area and initial pressure.

5. The method of claim 4 wherein said step of determining said permeability comprises calculating $$\frac{K_\infty A t}{V_D \mu L} + I = -C_2 P_L + (C_2 b - .5C_1)\log (P_0^2 +$$

$$2bP_0 - P_L^2 - 2bP_L) - [C_2(P_0^2 + 2bP_0 + 2b^2) -$$

$$(C_1 b + C_0)] \frac{\left[\tanh^{-1}\frac{(-P_L - b)}{(P_0 + b)}\right]}{(P_0 + b)}$$

where
- $K_\infty$ = Klinkenberg permeability
- $C_0, C_1, C_2$ = coefficients of $P_L$ from approximation of $F(P_L)$ which is a coefficient of flow that accounts for the overall effect of variable mass flow
- $P_0$ = pressure at upstream end of sample
- $P_L$ = pressure at downstream end of sample
- b = Klinkenberg slip (in atmospheres)
- A = cross-sectional area of core sample
- $V_D$ = said closed volume
- $\mu$ = viscosity of said fluid
- L = length of said core sample
- t = time
- I = integration constant.

6. A method of measuring the permeability of a core sample, comprising the steps of applying a fluid of predetermined test pressure to an upstream end of the core sample while the downstream end of said core sample exits to a closed volume and while a predetermined constant confining pressure is applied to said core sample; obtaining samples of the pressure at the downstream end of said core sample; obtaining samples of the time duration between pressure samples that differ from each other by a predetermined amount; detecting when the downstream pressure reaches a predetermined proportion of said test pressure; selecting a portion of the pressure and time samples obtained prior to said downstream pressure reaching said predetermined proportion; and determining said permeability as a function of the selected pressure and time samples.

7. The method of claim 6, wherein said selected portion of the pressure and time samples are those samples which were obtained while said downstream pressure changed by a selected quantity prior to reaching said predetermined proportion.

8. The method of claim 7 wherein, said selected quantity is a final downstream pressure change of 0.2 atmospheres prior to reaching said predetermined proportion.

9. The method of claim 6, wherein said selected portion of the pressure and time samples is approximately the last half of those samples which were obtained while said downstream pressure changed from an initial pressure thereof to said predetermined proportion.

10. The method of claim 6, wherein said selected portion of the pressure and time samples is the greater of either the number of samples which were obtained while said downstream pressure changed by approximately 0.2 atmospheres immediately prior to reaching said predetermined proportion or the last half of those samples which were obtained while said downstream pressure changed from an initial pressure thereof to said predetermined pressure.

11. The method of claim 6 further comprising the step of constraining the pressure and time sampling such that maximum and minimum numbers of pressure and time samples are obtained.

12. The method of claim 11 wherein said step of sampling the time duration comprises obtaining a time sample when said downstream pressure changes by approximately 0.05 psi; and said step of constraining the pressure and time sampling comprises obtaining samples of said downstream pressure and time at a rate no greater than one pressure and one time sample approximately every 0.875 psi.

13. A method of measuring the permeability of a core sample, comprising the steps of applying a fluid of predetermined test pressure to an upstream end of the core sample while the downstream end thereof exits to a closed volume and while a constant predetermined confining pressure is applied to said core sample; sampling the pressure at the downstream end of said core sample; sampling the passage of time for the downstream pressure to change by a predetermined amount; sensing when a predetermined number of time samples has been obtained; terminating the sampling of pressure and time when said downstream pressure reaches a predetermined proportion of said test pressure after said predetermined number of time samples has been obtained; selecting a portion of said pressure and time samples; and determining said permeability as a function of said selected portion of samples.

14. The method of claim 13 wherein said step of sampling the passage of time comprises obtaining no more than a first predetermined number of pressure samples per increment of pressure regardless of time; and said step of sampling the pressure includes obtaining a sample of downstream pressure when a time sample is obtained.

15. A method of measuring the permeability of a core sample held in a core sample holder of the type having an internal chamber in which said core sample is held and first and second channels extending into said chamber in fluid communication with opposite ends of said core sample, said method comprising the steps of abruptly changing the pressure by a predetermined amount in said first channel; measuring the pressure in said second channel caused by the abrupt change in pressure in said first channel; sensing when said pressure in said second channel attains predetermined values in response to said abrupt change in the pressure in said first channel; detecting the passage of time as said pressure in said second channel reaches said predetermined values; selecting only a portion of the pressure changes which are sensed and the passage of time which is detected prior to said pressure in said second channel reaching a predetermined proportion of the abrupt change of the pressure in said first channel; and determining said permeability as a function of the selected pressure changes and passage of time.

16. The method of claim 15 wherein said selected portion of pressure changes and passage of time comprises that portion of the pressure changes and passage of time which occur during the second half of an interval which commences with said abrupt change in the pressure in said first channel and which terminates when said pressure in said second channel reaches said predetermined proportion.

17. The method of claim 15 wherein said selected portion of pressure changes comprises those cumulative pressure changes which substantially equal either a final pressure change of approximately 0.2 atmospheres or the last half of the pressure changes, whichever is greater.

18. Apparatus for use in measuring the permeability of a core sample, comprising a core sample holder having an internal chamber for containing said core sample; a source of constant, predetermined confining pressure; means for supplying said confining pressure to said internal chamber; a source of predetermined test pressure substantially less than said confining pressure; a first channel communicating between said source of test pressure and said internal chamber for supplying said test pressure to an upstream end of said core sample; a second channel communicating with a downstream end of said core sample in said internal chamber and comprising at least a portion of a fixed closed volume; pressure transducer means disposed in said closed volume for producing electrical pressure signals representing the downstream pressure of said core sample; time sampling means for producing time samples, representing the passage of time; valve means coupled between said source of test pressure and said first channel and operative to apply said test pressure to said first channel; means for initiating said time sampling means when said valve means commences operation; means coupled to said pressure transducer means for detecting when the downstream pressure reaches a predetermined proportion of said test pressure; means for selecting a portion of the electrical pressure signals and time samples produced prior to said downstream pressure reaching said predetermined proportion; and means for determining the permeability of said core samples as a function of said selected electrical pressure signals and time samples.

19. The apparatus of claim 18 wherein said means for determining the permeability of said core sample comprises pressure sampling means for producing pressure samples of said electrical pressure signals in response to said time samples; and wherein said selecting means includes means for selecting the time samples produced when said downstream pressure changes by a predetermined increment and for selecting the time samples produced at a minimum rate and the pressure samples produced in response thereto when the first-mentioned time samples are produced at a rate less than said minimum rate.

20. The apparatus of claim 18 wherein said selecting means selects the electrical pressure signals and time samples produced during approximately the latter half of the interval between the time said valve means operates and the time said downstream pressure reaches said predetermined proportion.

* * * * *